United States Patent [19]

Dickakian

[11] Patent Number: 5,066,598

[45] Date of Patent: Nov. 19, 1991

[54] METHOD OF CHARACTERIZING THE EFFECTIVENESS OF BASEOIL ADDITIVES

[75] Inventor: Ghazi B. Dickakian, Houston, Tex.

[73] Assignee: Exxon Chemical Patents, Inc., Linden, N.J.

[21] Appl. No.: 425,421

[22] Filed: Oct. 23, 1989

Related U.S. Application Data

[62] Division of Ser. No. 876,460, Jun. 20, 1986, Pat. No. 4,897,176.

[51] Int. Cl.$^5$ ............... G01N 5/04; G01N 30/00; G01N 33/26

[52] U.S. Cl. .................... 436/2; 73/61.1 C; 73/61.2; 73/64; 436/60; 436/161; 436/181; 436/183

[58] Field of Search ............ 436/2, 60, 139–141, 436/161, 162, 174, 181, 183; 73/53, 61.1 C, 61.2, 64

[56] References Cited

U.S. PATENT DOCUMENTS

| | | | |
|---|---|---|---|
| 2,903,412 | 9/1959 | Longland | 208/41 |
| 4,048,056 | 9/1977 | Romovacek | 208/41 |
| 4,518,482 | 5/1985 | Dickakian | 208/44 X |
| 4,671,103 | 6/1987 | Dickakian | 73/61.1 C |
| 4,751,187 | 6/1988 | Dickakian | 436/60 |
| 4,752,587 | 6/1988 | Dickakian | 436/60 |
| 4,762,797 | 8/1988 | Dickakian | 436/60 |
| 4,849,361 | 7/1989 | Dickakian | 436/60 X |

Primary Examiner—Robert J. Hill, Jr.
Attorney, Agent, or Firm—M. B. Kapustij; V. T. White

[57] ABSTRACT

A process for preparing a baseoil blend of predetermined coking tendency, and for measuring the effectiveness of additives for reducing coking tendency in baseoils, utilizing the relationship of the content of volatile fractions and low boiling fractions in baseoil to the onset and/or progression of asphaltene formation.

19 Claims, 8 Drawing Sheets

METHOD OF CHARACTERIZING THE EFFECTIVENESS OF BASEOIL ADDITIVES

This is a division of application Ser. No. 876,460, filed June 20, 1986, now U.S. Pat. No. 4,897,176.

BACKGROUND OF THE INVENTION

1. Field of Invention

The invention relates to a process for preparing a blend of baseoils having a predetermined coking tendency, as well as to baseoil blends produced thereby. The invention further relates to a process for characterizing the effectiveness of baseoil additives used to reduce baseoil coking tendency.

2. Description of Background Materials

A number of standardized procedures exist for determining the coking tendencies of oils.

U.S. Pat. No. 3,248,327 discloses one test known as the Coker Detergency Test. This test is a modification of the Pratt and Whitney Test as described in United States Air Force Military Specification MIL-L-7808A. The test involves splashing the test oil in an air atmosphere against a heated aluminum panel for a given period of time and thereafter determining the amount of deposit formed on the panel. The oil is splashed onto the underside of an aluminum panel, and after a set period of time the test is stopped, and the aluminum panel is washed to remove excess non-coked oil. It is assumed that any increase in weight of the panel, after washing and drying, must be due to coke formation on the aluminum.

A similar technique is disclosed in U.S. Pat. Nos. 3,095,377 and 3,153,622, and is identified as a Panel Coker Test meeting United States Air Force specification MIL-L-9236A.

Yet another test is disclosed in U.S. Pat. Nos. 2,812,319 and 2,716,089, in which oil is heated and stirred in an aluminum measuring cup for a set period of time, after which the heated oil is permitted to settle without stirring. Thereafter the cycle is repeated a number of times, after which the oil is poured out of the cup, and the cup weighed to determine any increase in weight which would be indicative of coking.

Despite providing information as to the amount of coke which is formed, the above techniques are by their very definition imprecise and clumsy. These tests are subject to inconsistent results because of the numerous mechanical manipulations which are involved. Furthermore, none of the above techniques relies upon the measurement of asphaltenes as being an indicator of the coking tendencies of lubricating baseoils, but rather rely only upon the direct measurement of coke deposits.

SUMMARY OF THE INVENTION

One embodiment of the invention is broadly directed to a process for preparing a baseoil blend having a predetermined coking tendency, by:

(a) measuring the amount of volatile fractions, or low boiling fractions, or both, in each of the baseoils comprising the blend, to determine the onset and/or progression of asphaltene formation in each of these baseoils; and (b) blending at least two of the baseoils in relative proportions necessary to produce a blend having the desired coking tendency.

This embodiment may further include the step of measuring the amount of volatile fractions, or low boiling fractions, or both, present in the blend, for the purpose of determining the onset and/or progression of $C_7$-asphaltene formation.

The asphaltene for which onset and/or progression of formation is determined is, most preferably, $C_7$-asphaltene.

Step (a) can be carried out as to the volatile fractions by:

I. heating, to approximately 600° C., or to approximately 1,000° C., a sample of each of the baseoils, each sample comprising approximately 0.005 to 1.0g of baseoil, in a thermal balance and under an inert atmosphere, at a rate of approximately 5° to 20° C./min. or, more preferably, 10° C./min.; and II. continuously measuring the weight loss in each of the samples.

Step (a) can be carried out as to the low boiling fractions by gas chromatographic distillation.

These same means for measuring the volatile fractions and low boiling fractions can also be employed in the previously mentioned additional step for determining the coking tendency of the blend.

A second embodiment of the invention is broadly directed to a process for measuring the effectiveness of an additive for reducing the onset and/or progression of asphaltene formation in a baseoil, by:

(a) measuring the amount of volatile fractions, or low boiling fractions, or both, present in the baseoil to determine onset and/or progression of asphaltene formation in the absence of the additive;

(b) incorporating the additive into a sample of the baseoil, and characterizing its coking tendency by:

I. subjecting the sample to conditions which accelerate asphaltene formation in the baseoil; and II. testing for the onset and/or progression of asphaltene formation in the sample as a function of time; and (c) comparing the onset and/or progression of asphaltene formation in steps (a) and (b).

The previously discussed means for measuring volatile fractions and low boiling fractions can also be employed in this embodiment of the invention to determine the onset and/or progression of asphaltene formation in the absence of the additive.

Asphaltene formation can be accelerated in step (b) by any of several means.

One means comprises oxidizing and heating the baseoil, preferably by continuous oxidation at approximately 240°–360° C.

A second means for accelerating asphaltene formation is catalytic reaction of the baseoil. Any suitable catalyst, such as a Friedel-Craft catalyst, may be employed. The preferred catalyst is selected from the group consisting of ferric chloride hexahydrate, cobalt octoate, iron naphthenate, stannic chloride, and mixtures thereof. Most preferably, this catalytic reaction is carried out at a temperature of 180°–280° C.

A third means for accelerating asphaltene formation comprises reacting the baseoil with a material selected from a group consisting of peroxides, hydroperoxides, oxidized lube oils, and mixtures thereof. Any of these materials can also be added in the previously discussed catalytic reaction.

Any of these means for accelerating asphaltene formation can further include sparging the baseoil with an oxidizing gas selected from the group consisting of air, oxygen, ozone, nitrogen oxides (including nitric oxide), sulfur oxides, and mixtures thereof; preferably, the baseoil is sparged with air at 1–10 standard cubic feet of air per hour. Most preferably, a mechanical agitator is used to agitate the baseoil during this sparging.

DETAILED DESCRIPTION OF THE INVENTION

Analysis of used lube oils from engine tests and the carbonaceous materials from engine piston walls indicates that these materials have very high oxygen content. 2-3 wt.% of oxygen was found in the used lube oils, and 25-35 wt.% of oxygen was found in the carbonaceous material on the piston walls.

High oxygen content in the oil and the carbonaceous material indicates that oxidative-polymerization of the baseoils is responsible for the formation of the carbonaceous material in the lube oil and the deposition on the wall of the piston.

Further investigation of the mechanism of the carbon formation in lube oils led to the discovery that, on air oxidation of a baseoils, paraffin-insoluble compounds-asphaltenes- are the first molecular species formed in baseoils upon oxidation, and that these asphaltenes are transformed gradually into carbonaceous material containing high infusable coke (quinoline insolubles). Amongst the wide range of paraffin insolubles which are formed upon heating and oxidation, the heptane insolubles, hereinafter designated as $C_7$-asphaltenes, are of particular interest.

Asphaltenes generally are composed of carbon, hydrogen, oxygen, and sulfur, with a C:H atomic ratio of 1.0-1.5, and an average molecular weight of about 250-1,000. They are brownish solids with melting points of 100°-400° C., with extremely high tendency to coke formation at 200°-300° C. in a non-oxygen nitrogen atmosphere, with a coke yield of 35-55% over 2 hrs. The asphaltenes have a decomposition temperature of about 400° C. as determined by thermogravimetric analysis in nitrogen.

During oxidative-polymerization of the baseoil at high temperatures, e.g., 240°-360° C,, portions of the baseoils will react with oxygen, leading to polymerization and introduction of various oxygen functional groups, such as phenolic, hydroxyl, carboxyl, ketones, aldehydes, ethers, etc. Other polar atoms such as sulfur and nitrogen are also present. These high molecular weight, highly oxidized molecules become insoluble in aliphatic solvents, and can be determined quantitatively as the insolubles in paraffinic solvents. This insoluble portion is referenced herein as asphaltenes.

The carbonization of asphaltenes into various carbonaceous products and coke is known; for example, see U.S. Pat. No. 4,518,483, the disclosure of which is hereby incorporated by reference thereto, which teaches a process for carbonizing asphaltenes into carbon precursors useful for carbon fiber production.

The $C_7$-asphaltene formed during the oxidation of lube baseoil is defined as the insolubles in paraffinic solvents, and, more specifically, the insolubles in n-heptane. Therefore, asphaltenes represent a solubility class of compound.

Figure 7:
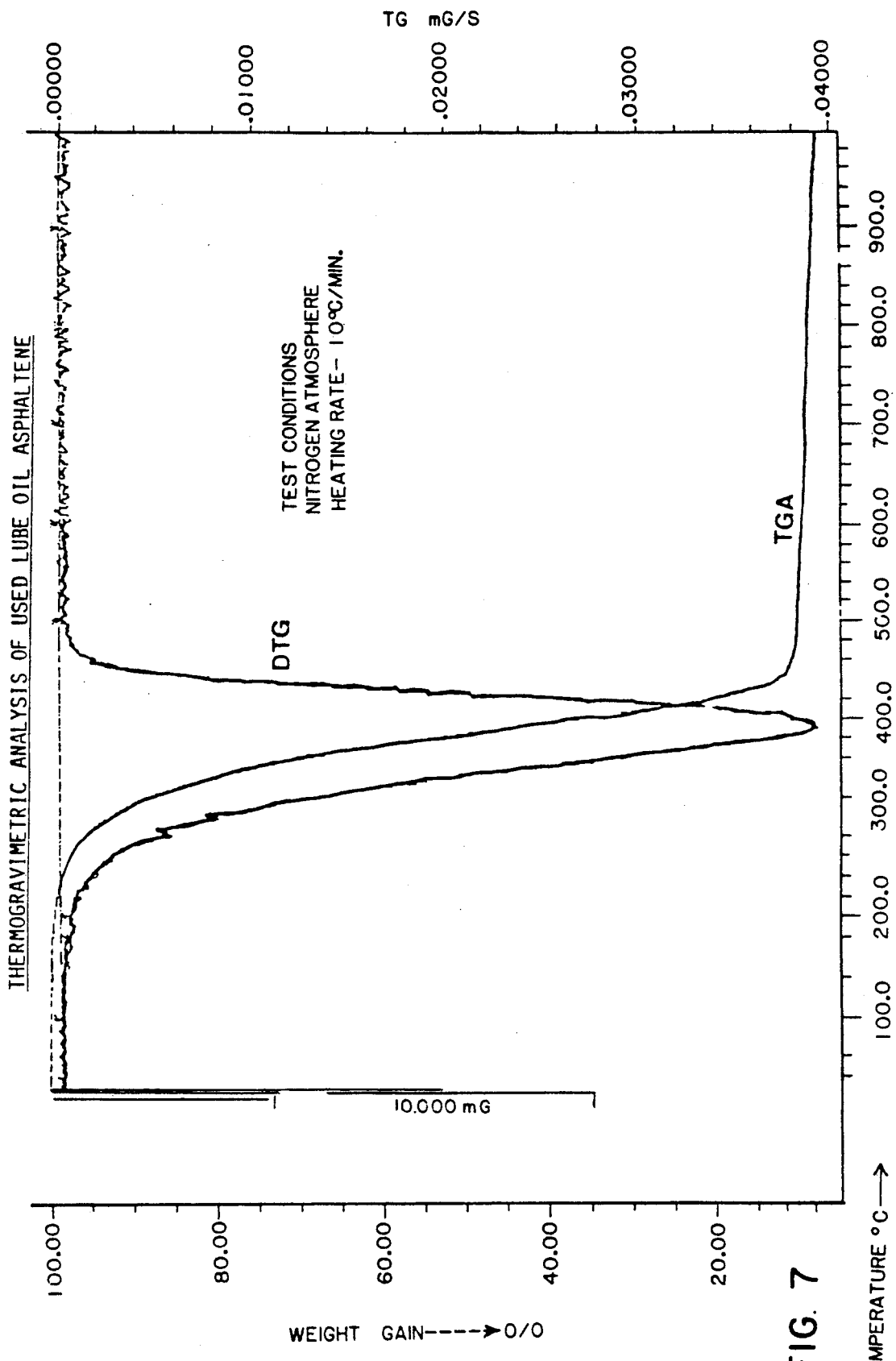
FIG. 7 illustrates the thermogravimetric analysis of asphaltene.

One method of characterizing asphaltenes is by thermogravimetric analysis (TGA). The thermogram of our $C_7$-asphaltenes is presented in FIG. 7 (showing maximum decomposition at about 400° C.).

Asphaltenes may be specified with reference to the particular paraffins in which they are insoluble, e.g., n-heptane, n-hexane, n-pentane, isopentane, petroleum ether, etc. For purposes of this application, particular reference is made to $C_7$-asphaltenes as being the preferred indicator for coke characterization purposes.

Figure 1:
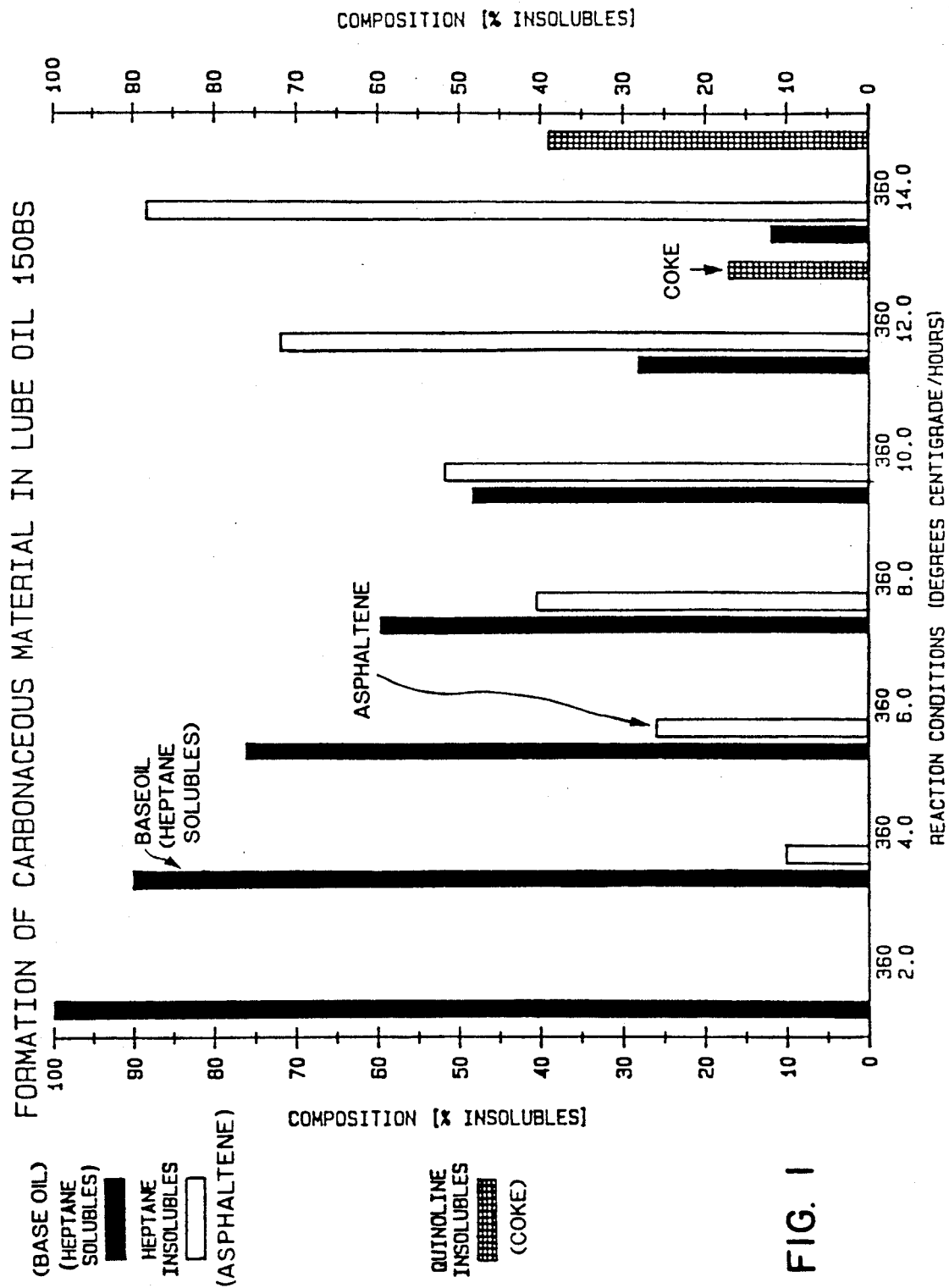
FIG. 1 illustrates the progression of asphaltene formation in a baseoil as a function of time at constant temperature.

The formation, in an initially asphaltene-free baseoil (150BS), of $C_7$-asphaltene and quinoline insolubles (coke) on subjecting the baseoil to air-oxidation at 360° C. (oil temperature) is illustrated graphically in FIG. 1. The transition from lube baseoil to substantially asphaltene (about 75%) prior to the onset of coke formation should be noted.

Figure 8:
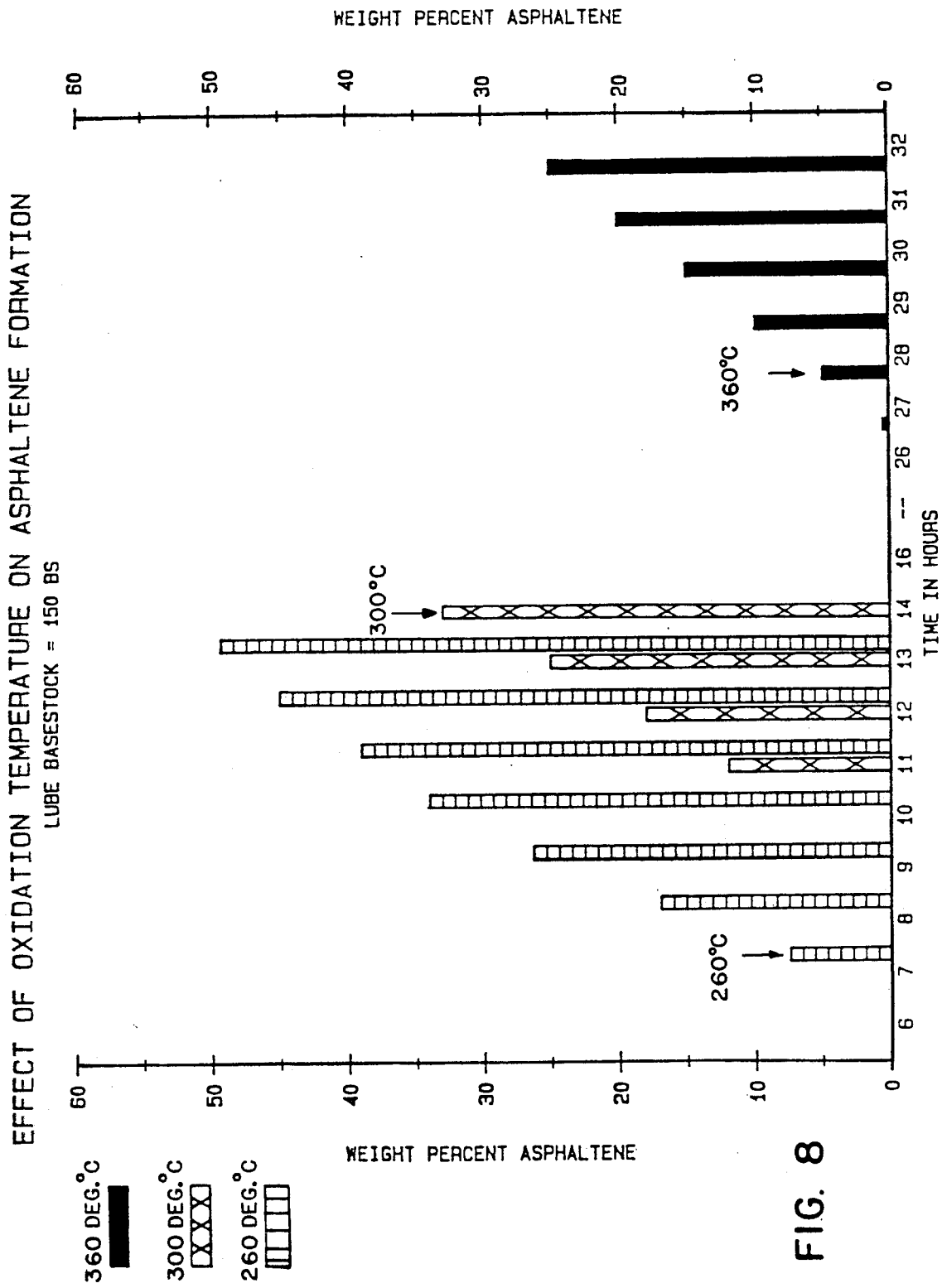
FIG. 8 illustrates the acceleration in onset and/or progression of asphaltene formation as a function of the temperature to which the baseoil is heated.

As further proof of the relationship between asphaltene and coking, reference is made to FIG. 8, in which it is seen that, as temperature increases, the onset of asphaltene formation, as is the case with coke formation, is accelerated.

Regarding $C_7$-asphaltene formation in baseoil oxidation, it has been discovered that the content of volatile fractions and/or low boiling fractions in the baseoil is directly related to asphaltene formation. Both embodiments of the invention are based upon the discovery of this relationship. In the first embodiment, this relationship is employed in a novel process for preparing a baseoil blend of predetermined coking tendency; in the second, it is the basis for a novel process for measuring the effectiveness of an additive for reducing the onset and/or progression of asphaltene formation in baseoil.

It is noted that the techniques of gas-chromatograph distillation and thermal analysis to measure boiling and volatilization rate, respectively, are standard methods of characterization. The novelty of the invention lies in the discovery of the relationship between the presence of volatile fractions and low boiling fractions in baseoils with the rate of $C_7$-asphaltene formation. It is the discovery of this relationship which allows for the new and unobvious processes for preparing baseoil blends of predetermined coking tendency, and for determining the effectiveness of additives for reducing the onset and/or progression of such asphaltene formation.

Basically, the inventive method of the first embodiment of this invention, for preparing the baseoil blend of predetermined coking tendency, involves two steps:

a. Measuring the amount of volatile fractions, or low boiling fractions, or both, present in each of the baseoils to be blended, in order to determine the onset and/or progression of asphaltene formation in each of the baseoils; and b. Blending at least two of the baseoils in the proper proportions for producing the blend of the desired coking tendency.

The volatile fractions present in the baseoils are quantitatively measured by means of thermal analysis, which measures the volatiles produced at 100° C.-600° C. Gas-chromatographic distillation is employed to quantitatively measure the presence of low boiling fractions.

A standard thermal balance is used for measuring the volatile fractions. A small quantity, approximately 0.005 to 1.0 grams, of a baseoil is heated in the thermal balance under nitrogen atmosphere from room temperature to 600° C., at a heating rate of from approximately 5° C./min. to 20° C./min. The most preferred heating rate is 10° C./min., for the reason that this rate provides a well-defined thermogram. During the heating, the weight loss occurring due to volatilization and decomposition of the baseoil is recorded continuously as a function of time.

Alternatively, the baseoil can be heated to 1,000° C. at the indicated heating rate, in either an inert or an oxidizing atmosphere.

Gas-chromatographic distillation (GC-D), is employed to measure the presence of low boiling fractions. A small sample of baseoil is injected into a chromatographic column. This column is then heated, and the boiling characteristics of the baseoil fractions are recorded.

These techniques of thermal analysis and gas-chromatograhic distillation can be applied to each of the baseoils which might be added to the blend. The resulting measurements can are used to determine the onset and/or progression of asphaltene formation in each of these baseoils. This information is subsequently used to determine the relative proportions of the baseoils to combine in order to produce a blend having the desired coking tendency. The relationship of baseoil low boiling fractions and volatile fractions to asphaltene formation, and therefore to coking tendency, is illustrated in the following examples.

EXAMPLES 1-4

Asphaltene Formation in Untreated Baseoil

Four baseoils obtained by vacuum distillation of vacuum residues are oxidized at 300° C. The asphaltene content is determined on samples obtained hourly and analyzed. The rate of $C_7$-asphaltene formation varies depending on the type of baseoil used.

The results of this procedure are indicated in Table 1 below.

TABLE I

| Oxidation Time (hours) | Example 1 Baseoil (100 N) | Example 2 Baseoil (150 LP) | Example 3 Baseoil (600 N) | Example 4 Baseoil (150 BS) |
|---|---|---|---|---|
| 1 | 0 | | | |
| 2 | 1.3 | 0 | | |
| 3 | 9.0 | 2.5 | | |
| 4 | 22.8 | 13.4 | | |
| 5 | 35.3 | 31.7 | | |
| 6 | 43.0 | 43.0 | 0 | |
| 7 | | | 0.9 | |
| 8 | | | 6.6 | 0 |
| 9 | | | 14.8 | 0.4 |

TABLE I-continued

| Oxidation Time (hours) | Example 1 Baseoil (100 N) | Example 2 Baseoil (150 LP) | Example 3 Baseoil (600 N) | Example 4 Baseoil (150 BS) |
|---|---|---|---|---|
| 10 | | | 28.2 | 5.0 |
| 11 | | 40.5 | | 12.0 |
| 12 | | | | 18.0 |
| 13 | | | | — |
| 14 | | | | 33.0 |
| 15 | | | | |
| 16 | | | | |

Figure 2:
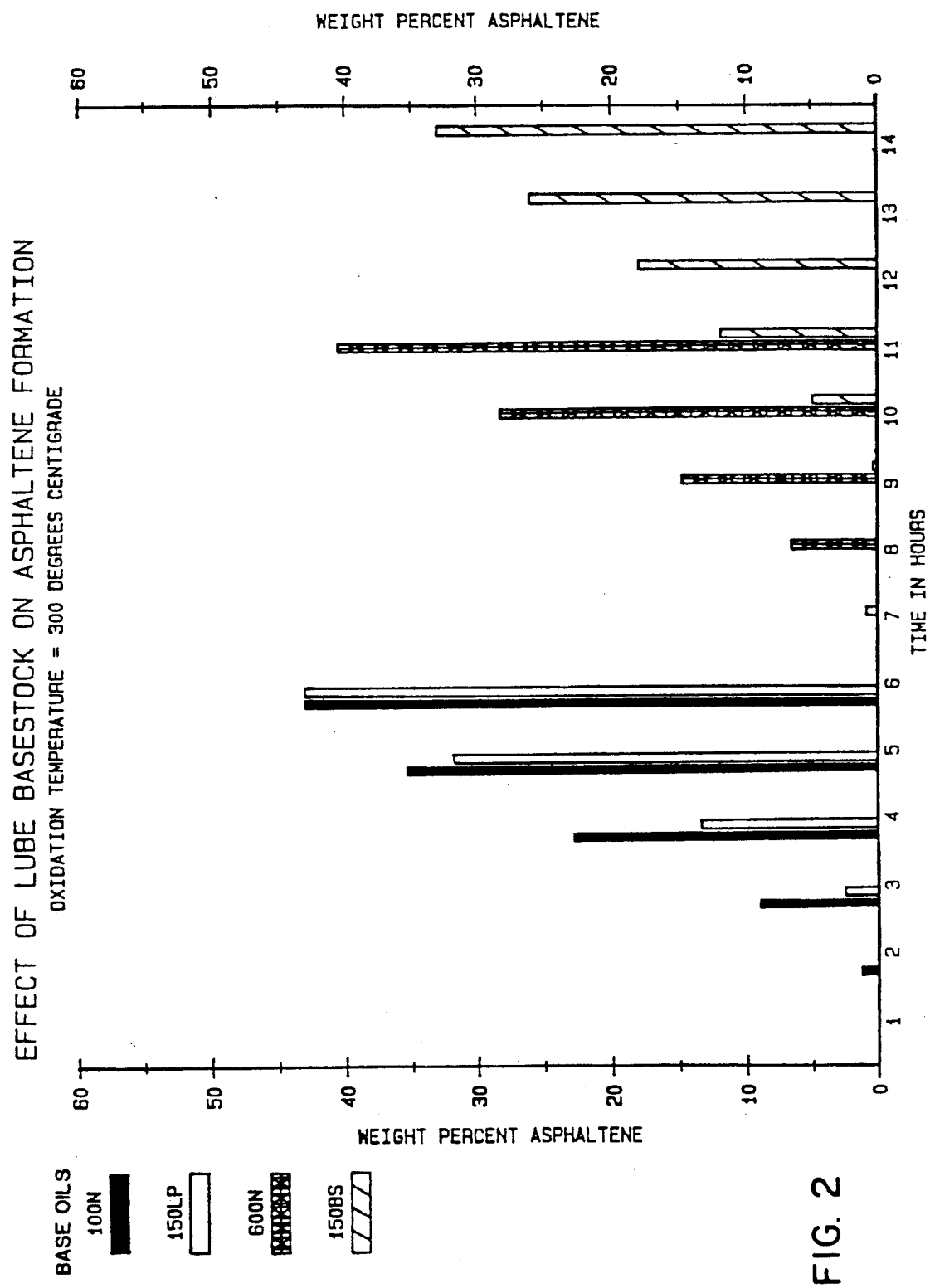
FIG. 2 comparatively illustrates the amounts of asphaltene as determined by gas-chromatographic distillation formed in different baseoils during oxidation, also as a function of time at constant temperatures FIG. 3 comparatively illustrates the volatilization characteristics of different baseoils in gas-chromatographic distillation as a function of temperature.

FIG. 2 graphically illustrates the results for Examples 1, 2, 3, and 4.

EXAMPLES 5-8

Gas-Chromatographic Distillation (GC-D) Characteristics of Baseoils

Four lube baseoils are injected into a gas-chromatographic distillation unit and their distillation characteristics are thereafter determined.

Figure 3:
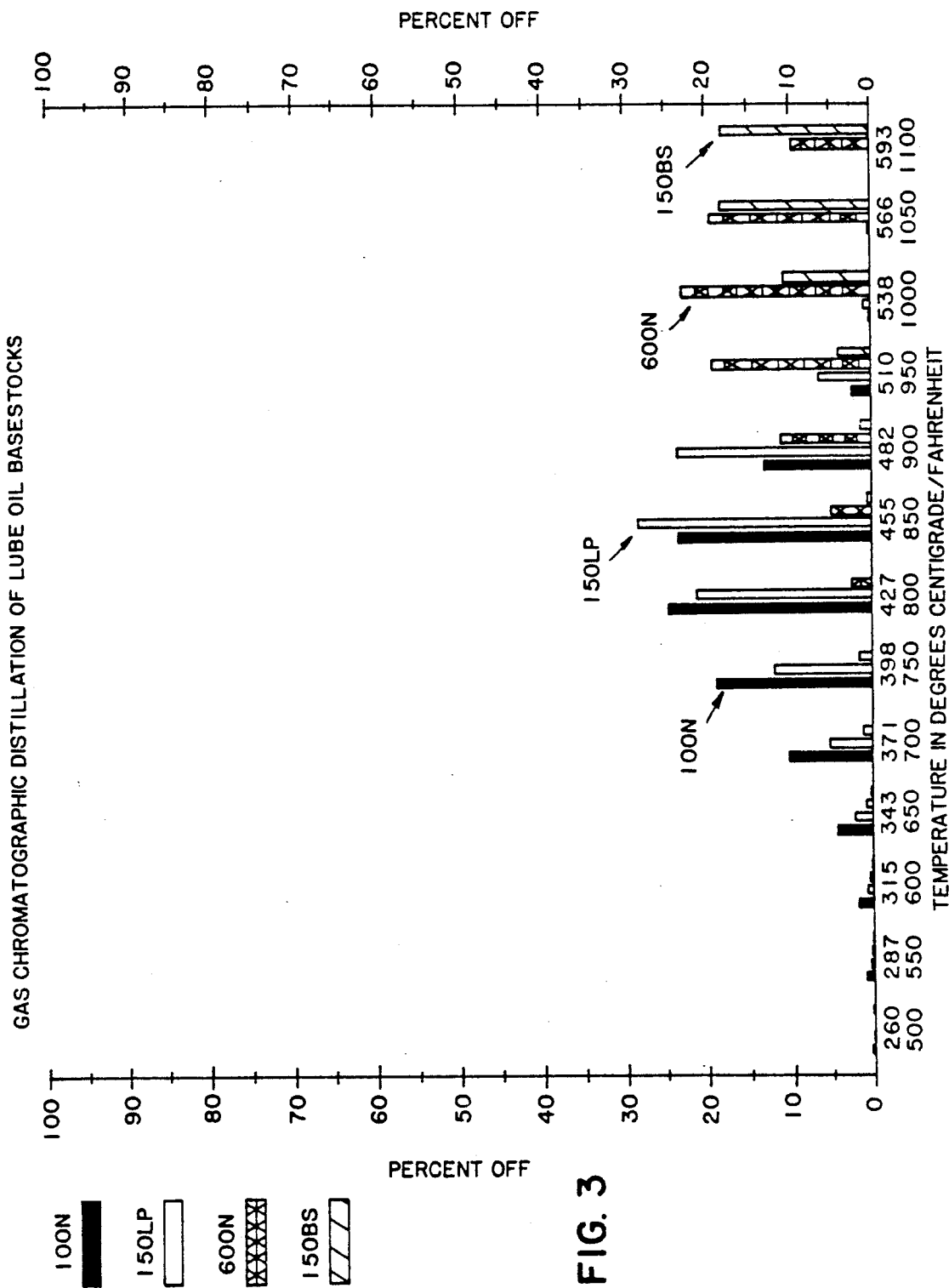

FIG. 3 illustrates the results of this characterization for Examples 5, 6, 7, and 8 for the four baseoils, 100N, 150BS, 600N, and 150LP, respectively.

EXAMPLES 9-12

Volatilization Characteristics of Baseoils by Thermogravimetric Analysis

Four baseoils are heated in a thermal balance, under nitrogen atmosphere (1.0 liter-min.), at a rate of 10° C./min., from room temperature to 500° C. The resulting weight loss at each temperature increment due to volatilization was automatically recorded, and is presented in Table II below.

TABLE II

| Temperature (°C.) | Example 9 Baseoil 100 N | Example 10 Baseoil 150 LP | Example 11 Baseoil 600 N | Example 12 Baseoil 150 BS |
|---|---|---|---|---|
| 150 | 1.0 | 0 | 0 | 0 |
| 175 | 1.0 | 1.0 | 0 | 0 |
| 200 | 6.5 | 4.0 | 1.0 | 0 |
| 225 | 11.5 | 7.5 | 0.5 | 0 |
| 250 | 25.0 | 17.5 | 2.0 | 1.0 |
| 275 | 20.0 | 15.0 | 4.5 | 0.5 |
| 300 | 33.0 | 50.0 | 5.0 | 2.0 |
| 325 | 0.5 | 3.5 | 10.0 | 4.5 |
| 350 | 0.5 | 0.5 | 23.0 | 5.5 |
| 375 | — | 0.5 | 20.0 | 6.5 |
| 400 | — | 0.5 | 30.5 | 14.0 |
| 425 | — | — | 3.5 | 16.0 |
| 450 | — | — | — | 30.8 |
| 475 | — | — | — | 18.0 |
| 500 | — | — | — | 2.0 |

Figure 4:
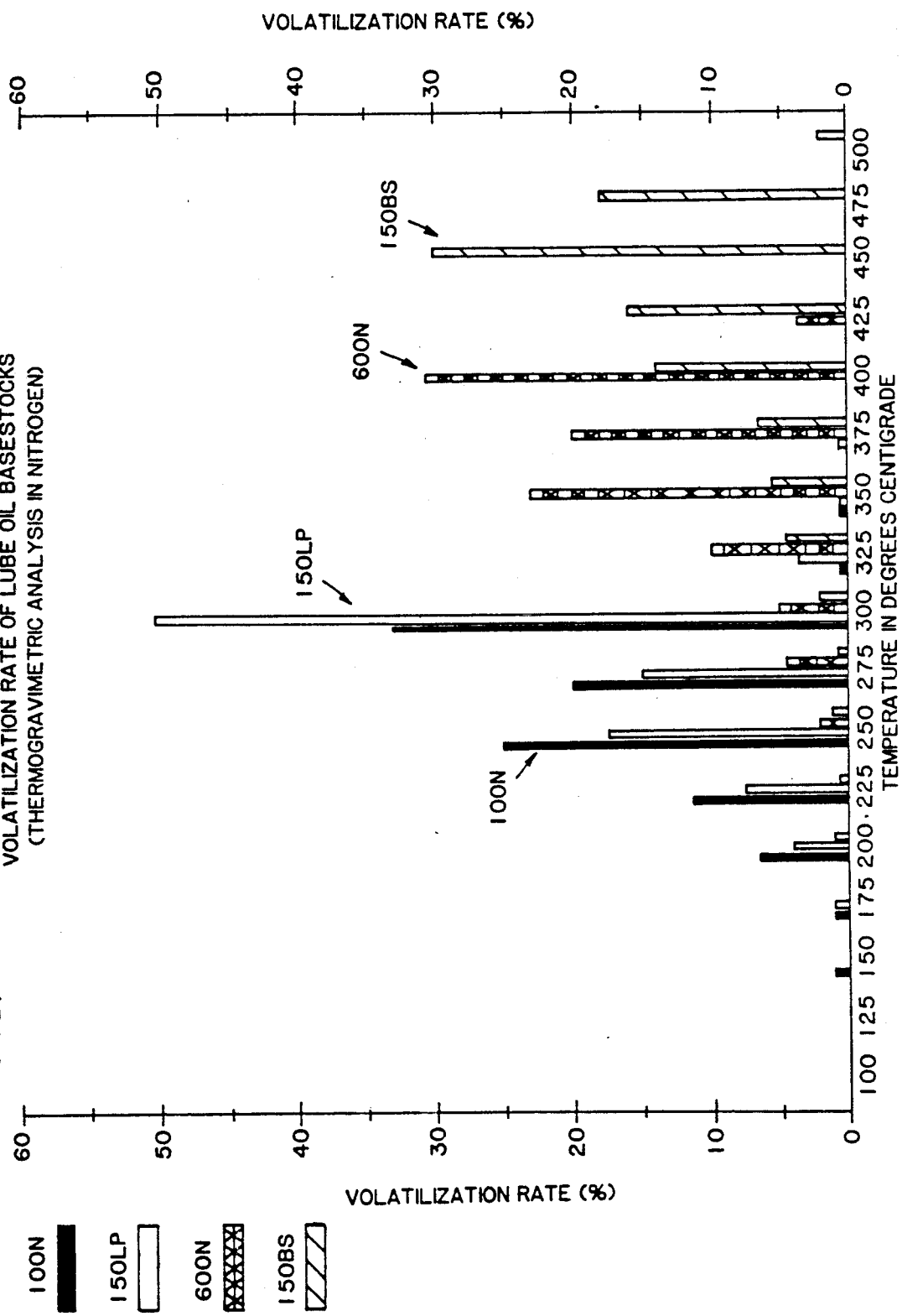
FIG. 4 comparatively illustrates the progressive weight loss in different baseoils at a rate of 10° C./min. from room temperature to 500° C. under nitrogen atmosphere as determined by thermogravimetric analysis.
Figure 5:
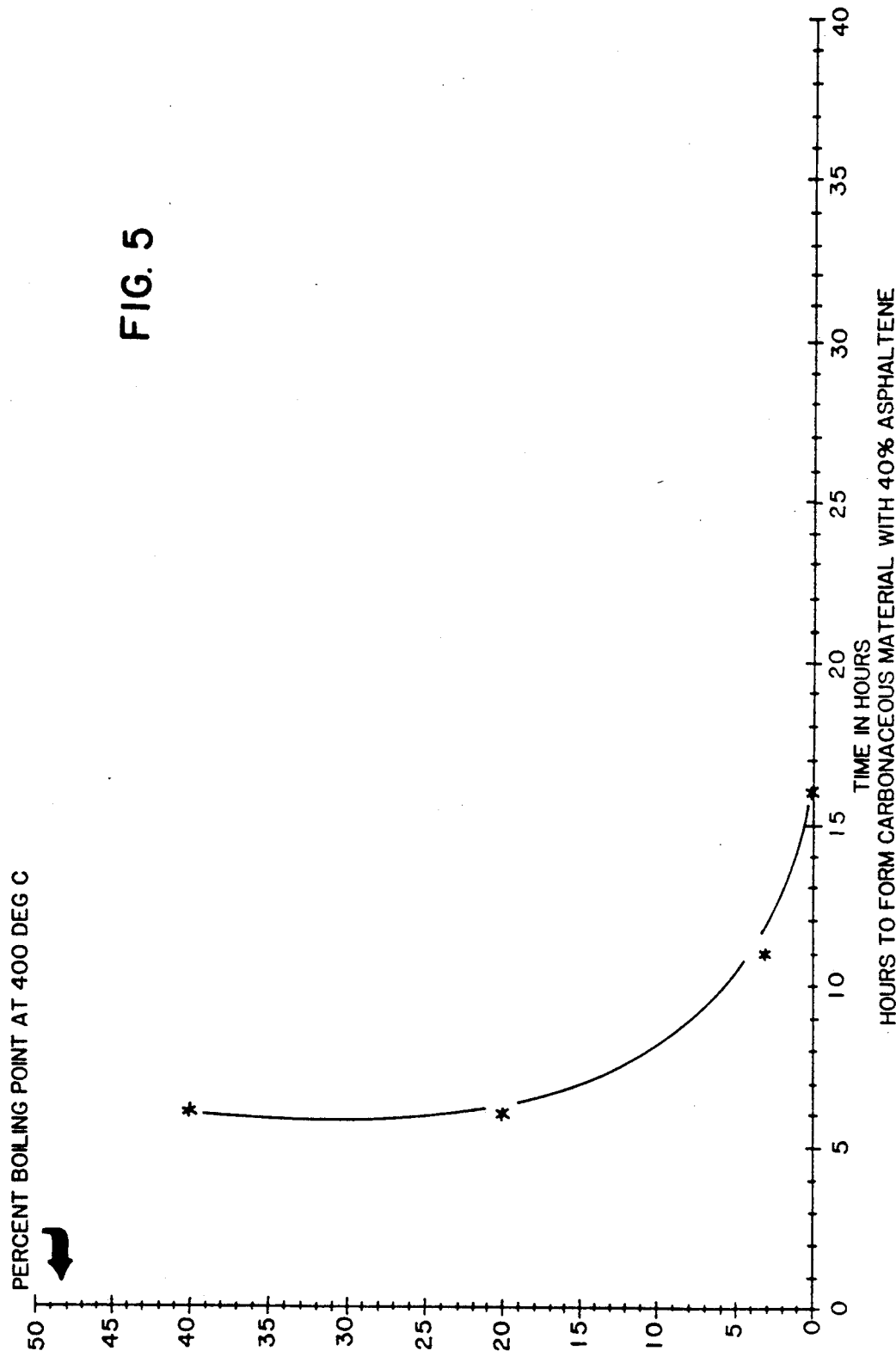
FIG. 5 illustrates the relationship of low boiling fractions, as determined by gas chromatographic distillation, to onset and/or progression of asphaltene formation in baseoils.
Figure 6:
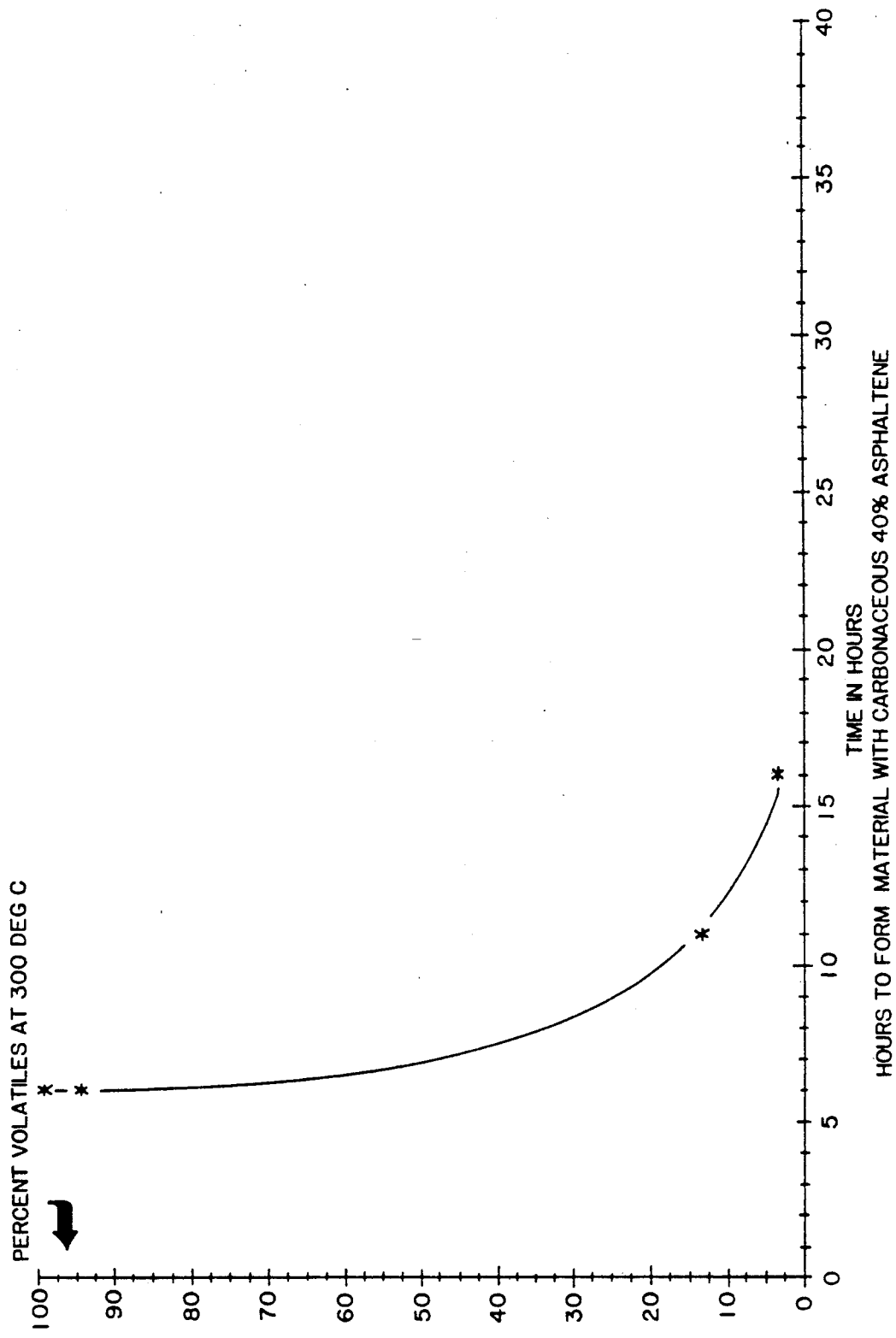
FIG. 6 illustrates the relationship of volatile fractions as determined by thermogravimetric analysis to onset and/or progression of asphaltene formation in baseoils.

The results of this procedure are graphically illustrated in FIG. 4.

EXAMPLES 13-16

Relation of Baseoil Low Boiling Fractions and Volatile Fractions to $C_7$ Asphaltene Formation The relationship of baseoil low boiling fractions (as determined by gas-chromatographic distillation), and of baseoil volatile fractions (as determined by thermal analysis), to the rate of asphaltene formation can be expressed by many methods.

One of these methods involves oxidizing baseoils at 300° C., and plotting the formation of low boiling fractions or volatile fractions against the time required to form a carbonaceous material containing 40% of $C_7$- asphaltenes. As presented below in Table IV, Examples 13-16 illustrate this relationship.

TABLE III

| Example | Baseoil Type | Thermal Analysis Volatiles @ 300° C. (wt %) | Gas-Chromatographic Fraction (%) with Boiling at 400° C. | Hours to form carbonaceous material with 40% of $C_7$-asphaltene |
|---|---|---|---|---|
| 13 | 100 N | 99 | 40 | 6 |
| 14 | 150 LP | 94 | 20 | 6 |
| 15 | 600 N | 13 | 3 | 11 |
| 16 | 150 BS | 3 | 0 | 16 |

The data presented above in Table III clearly demonstrate the relationship of amounts of low boiling fractions and volatile fractions in baseoils to coking tendencies. It is thus demonstrated that asphaltenes are the real precursors of coke formation.

MEASURING EFFECTIVENESS OF BASEOIL ADDITIVE

In co-pending application Ser. No. 876,462, now Pat. No. 4,849,361, attorney docket P4890, entitled "Method of Characterizing Coking Tendency of Baseoils", the disclosure of which is incorporated by reference, an inventive method for measuring the effectiveness of a baseoil additive for reducing the onset and/or progression of asphaltene formation in a baseoil is disclosed. In one embodiment, this inventive method comprises the steps of:

(a) subjecting a sample of a baseoil to conditions which accelerate asphaltene formation in the baseoil;

(b) testing for the onset and/or progression of asphaltene formation in the sample of a function of time;

(c) incorporating the additive to be tested into a second sample of the baseoil;

(d) subjecting this sample to asphaltene formation accelerating conditions substantially identical to those of step (a);

(e) testing for the onset and/or progression of asphaltene formation in the additive-containing baseoil of step (c) as a function of time under substantially identical conditions to step (b); and (f) comparing the onset times and/or formation rates measured in steps (b) and (e).

In the second embodiment of the invention, the steps of accelerating asphaltene formation, and testing for onset and/or progression of said formation, are replaced by the thermal analysis and gas-chromatic distillation techniques employed as part of the first embodiment of the invention, for preparing a blend of predetermined coking tendency.

Broadly stated, the inventive method of the second embodiment of this invention involves the steps of:

(a) measuring the amount of volatile fractions, or low boiling fractions, or both, present in the baseoil, to determine the onset and/or progression of asphaltene formation in the absence of the additive to be tested;

(b) incorporating the additive to be tested into a sample of the baseoil, and characterizing the coking tendency of the sample by the steps of:

I. subjecting the sample to conditions which accelerate asphaltene formation in the baseoil; and II. testing for the onset and/or progression of asphaltene formation in the sample as a function of time; and c. comparing the onset and/or progression of asphaltene formation in steps (a) and (b).

This embodiment of the invention provides the improvement of allowing the coking tendency of the additive-free baseoil sample to be determined without the necessity of performing the actual acceleration and measuring of asphaltene formation.

As for the step of characterizing the coking tendency of the baseoil with additive added, the acceleration of asphaltene formation can be accomplished by any one of several means.

One of such means comprises oxidizing and heating the baseoil, preferably by continuous oxidation, at approximately 240°-360° C.

Another means for accelerating asphaltene formation in the additive-free baseoil comprises subjecting the baseoil to catalytic reaction. Any appropriate catalyst, such as Freidel-Craft catalyst can be employed. Preferred catalysts include ferric chloride hexahydrate, cobalt octoate, iron naphthenate, stannic chloride, or mixtures of such catalysts. The catalyst is preferably employed in total amounts by weight of about 0.25% catalyst/fee. The catalytic reaction may be conducted at a temperature of approximately 180°-280° C. A material selected from the group consisting of peroxides, hydroperoxides, oxidized lube oils, and mixtures of such materials may also be employed in the catalytic reaction.

While use of a catalytic system does accelerate oxidation, it represents a less accurate simulation of accurate operating conditions, by virtue of the presence of the catalysts, and the use of lower reaction temperature.

A third means for accelerating asphaltene formation comprises reacting the baseoil with an effective amount of material selected from the group consisting of peroxides, hydroperoxides, oxidized lube oils, and mixtures of such materials.

Any of these three indicated means for accelerating asphaltene formation can further include sparging the baseoil with an oxidizing gas selected from the group consisting of air, oxygen, ozone, nitrogen oxides (such as nitric oxide), sulfur oxides, and mixtures of such oxidizing gases. Preferably, the sparging is conducted with air, as 1-10 standard cubic feet of air per hour. Most preferably, the baseoil is agitated by means of a mechanical agitator during the sparging.

Further, an inert gas such as nitrogen, carbon dioxide, helium, or mixtures of such gases may be incorporated into the oxidizing gas during the sparging.

Although the invention has been described with reference to particular means, materials and embodiments, it is to be understood that the invention is not limited to the particulars disclosed and extends to all equivalents within the scope of the claims.

What is claimed is:

1. A process for measuring the effectiveness of an additive for reducing the onset and/or progression of asphaltene formation in a baseoil, said process comprising:

(a) measuring the amount of volatile fractions and low boiling fractions present in said baseoil to determine, in the absence of said additive, the onset and/or progression of asphaltene formation in said baseoil;

(b) incorporating said additive into a sample of said baseoil, and characterizing the coking tendency of said sample by the steps of:
  I. subjecting said sample to conditions which accelerate asphaltene formation in said baseoil; and
  II. testing for the onset and/or progression of asphaltene formation in said sample as a function of time; and (c) comparing the onset and/or progression of asphaltene formation in steps (a) and (b).

2. The process of claim 1 wherein the asphaltene for which the onset and/or progression of formation is determined is $C_7$-asphaltene.

3. The process of claim 2 wherein step (a) comprises:
  I. measuring the amount of volatile fractions present in the said baseoil by the steps of:
    A. heating, to approximately 600° C., a sample comprising approximately 0.005 to 1.0g of said baseoil, under an inert atmosphere and in a thermal balance, at a rate of approximately 5° to 20° C./min.; and
    B. continuously measuring the weight loss in said sample; and
  II. measuring the amount of low boiling fractions present in said baseoil by gas chromatographic distillation.

4. The process of claim 3 wherein the heating rate in step (a) I.A. is 10° C./min., and the inert atmosphere comprises nitrogen.

5. The process of claim 2 wherein step (a) comprises:
I. measuring the amount of volatile fractions present in said baseoil by the steps of:
    A. heating, to approximately 1000°, a sample comprising approximately 0.005 to 1.0g of baseoil, under an atmosphere selected from the group consisting of inert atmospheres and oxidizing atmospheres and in a thermal balance, at a rate of approximately 5° to 20° C./min.; and
    B. continuously measuring the weight loss in said sample; and
  II. measuring the amount of low boiling fractions present in said baseoil by gas chromatographic distillation.

6. The process of claim 4 wherein asphaltene formation is accelerated in step (b) by oxidizing and heating said baseoil.

7. The process of claim 6 wherein asphaltene formation is accelerated in step (b) by continuous oxidation at approximately 240°-360° C. while sparging said baseoil with an oxidizing gas selected from the group consisting of air, oxygen, ozone, nitrogen oxides, sulfur oxides, and mixtures thereof.

8. The process of claim 7 comprising incorporating an inert gas into said oxidizing gas, said inert gas being selected from the group consisting of nitrogen, carbon dioxide, helium, and mixtures thereof.

9. The process of claim 7 comprising sparging said baseoil in step (b) with air at 1-10 standard cubic feet of air per hour.

10. The process of claim 7 comprising agitating said baseoil during said sparging with a mechanical agitator.

11. The process of claim 4 wherein asphaltene formation is accelerated in step (b) by catalytic reaction of said baseoil.

12. The process of claim 11 wherein said catalytic reaction is performed by exposing said baseoil to a catalyst selected from the group consisting of ferric chloride hexahydrate, cobalt octoate, iron naphthenate, stannic chloride, and mixtures thereof.

13. The process of claim 12 wherein said catalytic reaction is performed by further exposing said baseoil to a material selected from the group consisting of peroxides, hydroperoxides, oxidized lube oils,: and mixtures thereof.

14. The process of claim 12 comprising heating said baseoil during said catalytic reaction at a temperature of 180°-280° C.

15. The process of claim 11 comprising sparging said baseoil during said catalytic reaction with an oxidizing gas selected from the group consisting of air, oxygen, ozone, nitrogen oxides, sulfur oxides, and mixtures thereof.

16. The process of claim 15 comprising incorporating an inert gas into said oxidizing gas, said inert gas being selected from the group consisting of nitrogen, carbon dioxide, helium, and mixtures thereof.

17. The process of claim 4 wherein asphaltene formation is accelerated in step (b) by reacting said baseoil with a material selected from the group consisting of peroxides, hydroperoxides, oxidized lube oils, and mixtures thereof.

18. The process of claim 17 comprising sparging said baseoil during said reaction with an oxidizing gas selected from the group consisting of air, oxygen, ozone, nitrogen oxides, sulfur oxides, and mixtures thereof.

19. The process of claim 18 comprising incorporating an inert gas into said oxidizing gas, said inert gas being selected from the group consisting of nitrogen, carbon dioxide, helium, and mixtures thereof.

* * * * *